(12) United States Patent
Yanuma et al.

(10) Patent No.: US 10,478,044 B2
(45) Date of Patent: Nov. 19, 2019

(54) TREATMENT INSTRUMENT FOR ENDOSCOPE AND ENDOSCOPE SYSTEM

(71) Applicant: OLYMPUS CORPORATION, Tokyo (JP)

(72) Inventors: Yutaka Yanuma, Tokyo (JP); Madoka Kiyokawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 85 days.

(21) Appl. No.: 14/822,142

(22) Filed: Aug. 10, 2015

(65) Prior Publication Data
US 2015/0342633 A1  Dec. 3, 2015

Related U.S. Application Data

(63) Continuation of application No. PCT/JP2014/059829, filed on Apr. 3, 2014.

(30) Foreign Application Priority Data

Jun. 27, 2013 (JP) .................................. 2013-135458

(51) Int. Cl.
*A61B 1/00* (2006.01)
*A61B 17/3209* (2006.01)
(Continued)

(52) U.S. Cl.
CPC ...... *A61B 1/00087* (2013.01); *A61B 1/00098* (2013.01); *A61B 1/018* (2013.01);
(Continued)

(58) Field of Classification Search
CPC ........ A61B 17/00292; A61B 17/00296; A61B 17/0034; A61B 17/00353;
(Continued)

(56) References Cited

U.S. PATENT DOCUMENTS

| 4,619,263 A | * | 10/1986 | Frisbie | .................. | A61M 25/01 |
| | | | | | 600/585 |
| 4,686,963 A | * | 8/1987 | Cohen | .................. | A61B 1/0055 |
| | | | | | 138/120 |

(Continued)

FOREIGN PATENT DOCUMENTS

| EP | 2 025 298 A1 | 2/2009 |
| JP | 2004-527267 A | 9/2004 |

(Continued)

OTHER PUBLICATIONS

International Search Report dated Jun. 10, 2014 issued in PCT/JP2014/059829.

(Continued)

*Primary Examiner* — Ryan N Henderson
(74) *Attorney, Agent, or Firm* — Scully, Scott, Murphy & Presser, P.C.

(57) ABSTRACT

A treatment instrument for an endoscope used in combination with an endoscope having a raising base at a distal end section of a channel, the treatment instrument for the endoscope includes a sheath section having flexibility; a treatment section installed closer to a distal end side than the sheath section; and a manipulation unit installed at a proximal end of the sheath section and configured to manipulate the treatment section, wherein the sheath section has a sheath main body; a sandwiched portion formed at a distal end side of the sheath main body and sandwiched between the raising base and an inner circumferential surface of the channel; and a torque transmission member configured to transmit a rotational torque input at the proximal end side by a user and turn the sheath main body about the axis.

2 Claims, 16 Drawing Sheets

(51) Int. Cl.
  *A61B 17/32* (2006.01)
  *A61B 17/3205* (2006.01)
  *A61B 1/018* (2006.01)
  *A61B 18/14* (2006.01)
  *A61B 90/00* (2016.01)
  *A61B 17/00* (2006.01)
  *A61B 17/29* (2006.01)
  *A61B 18/00* (2006.01)
  *A61B 90/30* (2016.01)

(52) U.S. Cl.
  CPC ........ *A61B 17/32* (2013.01); *A61B 17/32002* (2013.01); *A61B 17/3209* (2013.01); *A61B 17/320016* (2013.01); *A61B 17/32056* (2013.01); *A61B 18/1492* (2013.01); *A61B 90/361* (2016.02); *A61B 2017/00526* (2013.01); *A61B 2017/00818* (2013.01); *A61B 2017/2929* (2013.01); *A61B 2017/320032* (2013.01); *A61B 2018/00982* (2013.01); *A61B 2018/141* (2013.01); *A61B 2090/309* (2016.02)

(58) Field of Classification Search
  CPC .... A61B 17/320024; A61B 17/320032; A61B 17/32004; A61B 1/00087; A61B 1/00098; A61B 1/018; A61B 1/012; A61B 17/320016; A61B 17/32002; A61B 17/00234; A61B 18/14; A61B 2018/1407; A61B 2018/141; A61B 2018/1412; A61B 2018/142; A61B 2018/144; A61B 17/32056; A61B 2017/320024; A61B 2017/320032; A61B 2017/32004
  USPC ........ 600/104, 106, 107, 114, 115, 139–152; 604/523–528
  See application file for complete search history.

(56) References Cited

U.S. PATENT DOCUMENTS

| | | | |
|---|---|---|---|
| 6,482,221 B1* | 11/2002 | Hebert | A61B 17/12022 606/194 |
| 7,371,237 B2 | 5/2008 | Hutchins et al. | |
| 2007/0270638 A1 | 11/2007 | Kitano et al. | |
| 2008/0221550 A1* | 9/2008 | Lee | A61M 25/10 604/508 |
| 2009/0048487 A1 | 2/2009 | Yanuma | |
| 2009/0156995 A1* | 6/2009 | Martin | A61B 50/30 604/95.04 |

FOREIGN PATENT DOCUMENTS

| | | |
|---|---|---|
| JP | 2005-334000 A | 12/2005 |
| JP | 2006-333996 A | 12/2006 |
| JP | 2007-330756 A | 12/2007 |
| JP | 2009-045451 A | 3/2009 |
| JP | 2010-088639 A | 4/2010 |
| WO | 02/13711 A1 | 2/2002 |
| WO | 2006/113465 A1 | 10/2006 |

OTHER PUBLICATIONS

Extended Supplementary European Search Report dated Nov. 11, 2016 in related European Patent Application No. 14 81 8816.2.
Japanese Office Action dated Feb. 7, 2017 in Japanese Patent Application No. 2013-135458.
Japanese Notice of Reasons for Rejection dated Jun. 19, 2018 received in Japanese Patent Application No. 2017-167838, together with an English-language translation.

* cited by examiner

TREATMENT INSTRUMENT FOR ENDOSCOPE AND ENDOSCOPE SYSTEM

This application is a continuation application based on a PCT International Application No. PCT/JP2014/059829, filed on Apr. 3, 2014, whose priority is claimed on Japanese Patent Application No. 2013-135458, filed on Jun. 27, 2013, both of the contents of the PCT International Application and the Japanese Patent Application are incorporated herein by reference.

BACKGROUND OF THE INVENTION

Field of the Invention

The present invention relates to a treatment instrument for an endoscope used in combination with an endoscope having a raising base formed at a distal end section of a channel, and an endoscope system including the treatment instrument for the endoscope.

Description of Related Art

When an endoscope is used to remove bile duct stones, since the duodenal papilla as an outlet port of the bile duct is narrowed, the stones may not be discharged as they are. In this case, the sphincter muscles are incised and the outlet port of the bile duct is widened to extract the stones with the treatment instrument for the endoscope passing through the endoscope, for example, a papillotome or the like as disclosed in Japanese Unexamined Patent Application, First Publication No. 2005-334000 and U.S. Pat. No. 7,371,237.

Since a position of a headband fold substantially coincides with a direction in which the bile duct extends around the duodenal papilla and the direction causes the blood vessel to be narrowed and the blood vessel does not easily bleed, in general, incision of the sphincter muscles is performed in the direction of the headband fold.

Here, in an endoscope appropriate for treatment of the liver and pancreas, when the endoscope is inserted into the duodenum to acquire an endoscope image, an image in which the bile duct is directed in substantially a twelve-o'clock direction is obtained. In such an endoscope, a raising base capable of elevating the papillotome in the twelve-o'clock direction is installed. Further, even in the papillotome used for incision of the sphincter muscles, when the papillotome protrudes from a distal end of the endoscope for the liver and pancreas, the papillotome is manufactured such that a direction of a knife portion (a treatment section) is automatically directed in substantially the twelve-o'clock direction of the endoscope screen.

Upon incision, the knife portion of the papillotome is stretched through manipulation of a near side. The knife portion is spaced apart from a sheath (a sheath section) and only the knife portion is pushed against the duodenal papilla. Accordingly, a large pressure occurs between the knife portion and a mucous membrane of the incised portion. When the raising base is driven while supplying electricity to the knife portion, a distal end of the papillotome is moved in the twelve-o'clock direction and the duodenal papilla is incised.

When the bile duct has a morphological feature or the like, when peripheral organs such as the duodenum or the like are narrowed, when a patient has received a surgical operation on a peripheral organ such as the duodenum or the like in the past, or the like, the direction of the bile duct in the vicinity of the duodenal papilla may be different from the twelve-o'clock direction of the endoscope screen.

Here, the papillotome of the related art is provided to easily perform the incision even in a direction other than the twelve-o'clock direction on the endoscope screen, and a torque transmission member configured to transmit a rotational torque from a hand is installed. Accordingly, the papillotome is configured to transmit a rotational torque for turning a proximal end side of the sheath about an axis to a distal end of the knife portion.

SUMMARY OF INVENTION

According to a first aspect of the present invention, a treatment instrument for endoscope used in combination with an endoscope having a raising base at a distal end section of a channel includes: a sheath section having flexibility; a treatment section installed closer to a distal end side than the sheath section; and a manipulation unit installed at a proximal end of the sheath section and configured to manipulate the treatment section, wherein the sheath section has: a sheath main body having a lumen extending along an axis of the sheath section; a sandwiched portion formed at a distal end side of the sheath main body and sandwiched between the raising base raised when the sheath main body is inserted into the channel and an inner circumferential surface of the channel; and a torque transmission member extending from a proximal end side of the sheath main body to the sandwiched portion in an axial direction of the sheath section and configured to transmit a rotational torque input at the proximal end side by a user and turn the sheath main body about the axis, and an outer diameter of the sandwiched portion is larger than a diameter of a maximum inscribed circle among inscribed circles of portions sandwiching the sandwiched portion between the raising base and the inner circumferential surface of the channel when the raising base is completely raised.

According to a second aspect of the present invention, in the endoscope of the first aspect, a forceps stopper configured to enable insertion of the sheath section and reduce leakage of a liquid from the channel may be installed at a proximal end section of the channel, the distal end side of the sheath section may be an integrated sheath region to which the torque transmission member is attached outside the outer circumferential surface of the sheath main body, the proximal end side of the sheath section may be a separated sheath region to which the torque transmission member is not attached outside the outer circumferential surface of the sheath main body, and in a state in which the treatment section protrudes from the distal end of the channel, the sheath section of the separated sheath region may be inserted through the forceps stopper.

According to a third aspect of the present invention, in the treatment instrument for the endoscope according to the second aspect, in the separated sheath region, the torque transmission member may be disposed in the lumen of the sheath main body.

According to a fourth aspect of the present invention, in the treatment instrument for the endoscope according to the second aspect, the sheath main body in the separated sheath region may have at least a first lumen and a second lumen, the torque transmission member may be disposed in the first lumen in the separated sheath region, and a slit reaching the outer circumferential surface of the sheath main body may be formed at the second lumen in the separated sheath region.

An endoscope system of a fifth aspect of the present invention includes the treatment instrument for the endoscope of the first aspect; and an endoscope having a channel configured to enable insertion of the sheath section of the treatment instrument for the endoscope and provided with a raising base formed at a distal end section.

According to a sixth aspect of the present invention, a method in which the treatment instrument for an endoscope is used in combination with the endoscope having a channel that is capable of being inserted into the sheath section according to claim 1 comprises: a step of passing the sheath section through the channel of the endoscope, and protruding the treatment section from the channel; a step of sandwiching the sandwiched portion of the sheath main body between the raising base which is raised and the inner circumferential surface of the channel; a step of turning the sheath main body about the axis of the sheath section to apply a rotational torque to the sheath main body, while observing the direction about the axis of the treatment section by the endoscope, as the torque transmission member is turned to a first side in the circumferential direction at the proximal end side of the torque transmission member; and a step of turning the torque transmission member to a second side different from the first side in the circumferential direction at the proximal end side of the torque transmission member and releasing the rotational torque applied closer to the proximal end side than the sandwiched portion of the sheath main body, when the treatment section is oriented in the desired direction.

DETAILED DESCRIPTION OF THE INVENTION

First Embodiment

Hereinafter, a first embodiment of the endoscope system according to the present invention will be described with reference to FIGS. 1 to 14 using the case in which a treatment instrument for an endoscope is a papillotome as an example.

Figure 1:
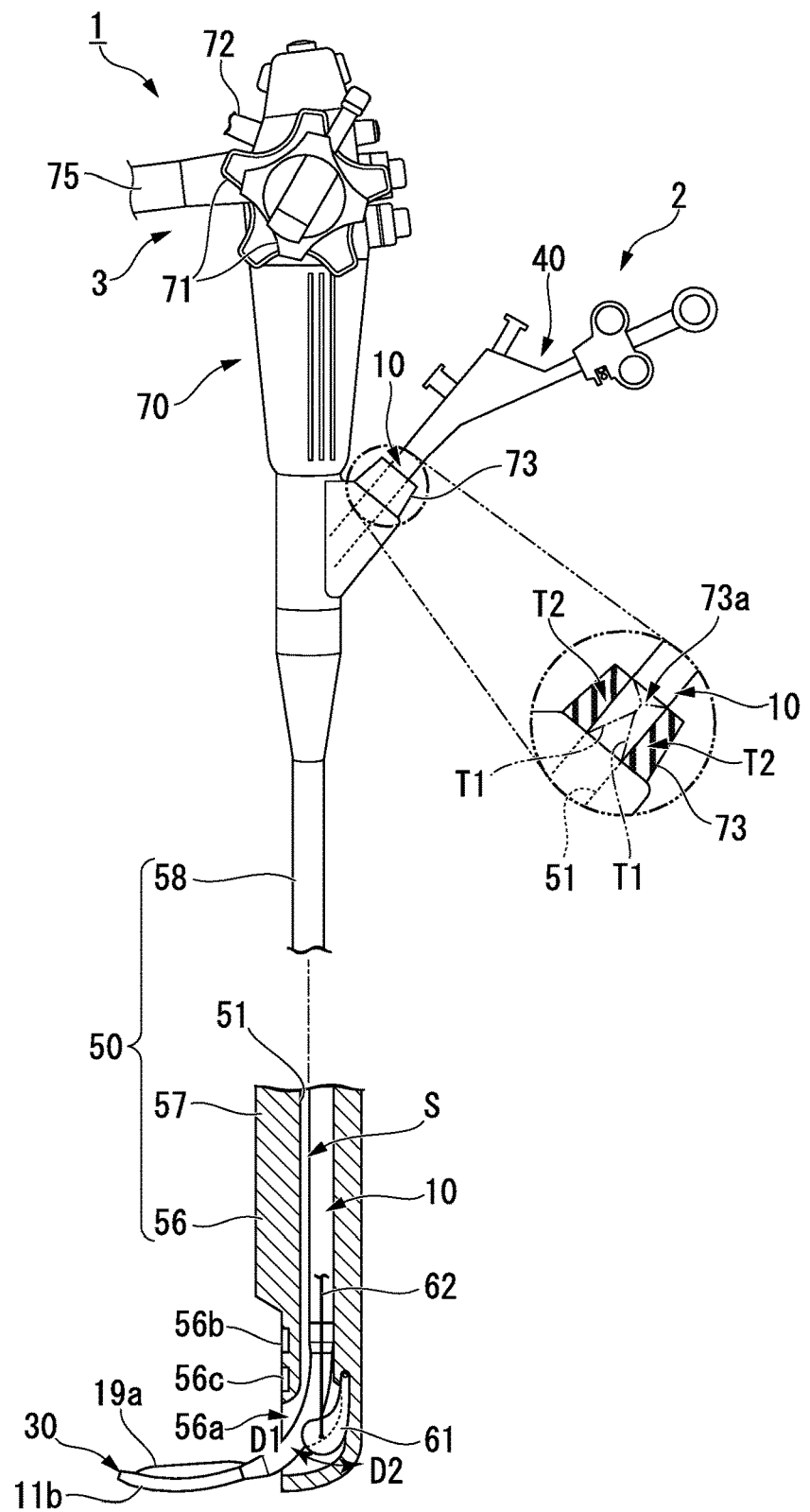
FIG. 1 is a general view showing an endoscope system of a first embodiment of the present invention, a portion of which is broken.

As shown in FIG. 1, an endoscope system 1 includes a papillotome 2 provided with an insertion section (a sheath section) 10 having flexibility, and an endoscope 3 having a channel 51 through which the insertion section 10 can be inserted. That is, the papillotome 2 is combined with the endoscope 3 and used therewith.

Figure 2:
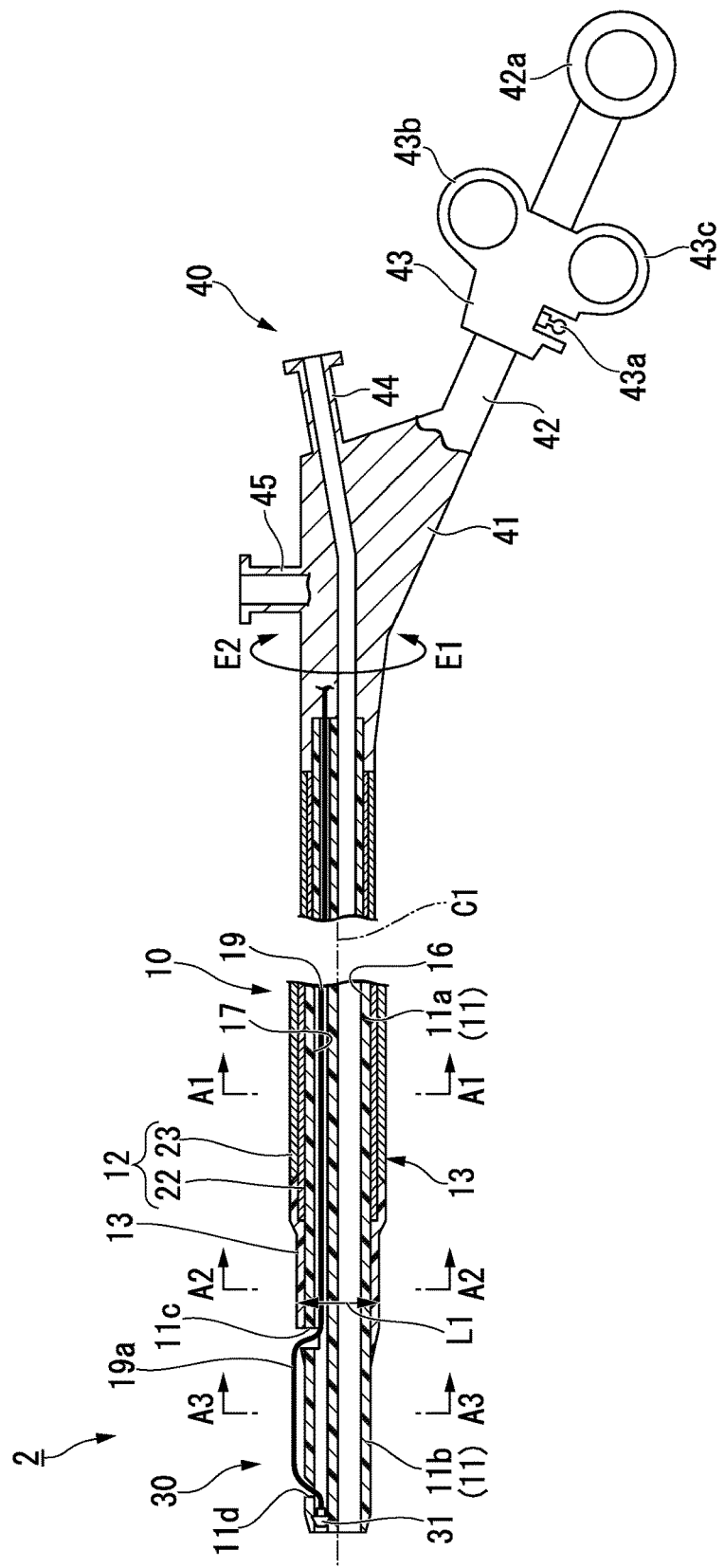
FIG. 2 is a view schematically showing a side surface of a papillotome of the endoscope system, a portion of which is broken.

As shown in FIGS. 1 and 2, the papillotome 2 includes the above-mentioned insertion section 10, a treatment section 30 installed closer to a distal end side than the insertion section 10, and a manipulation unit 40 configured to manipulate the treatment section 30 installed at a proximal end section of the insertion section 10.

Figure 3:
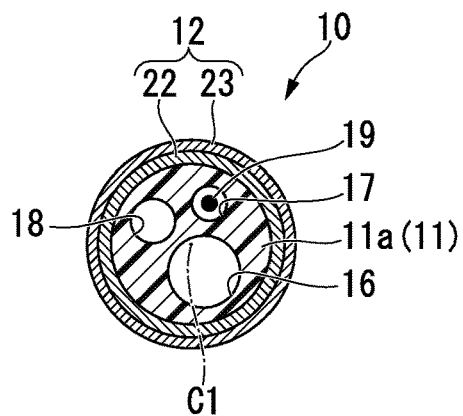
FIG. 3 is a cross-sectional view taken along line A1-A1 of FIG. 2.
Figure 4:
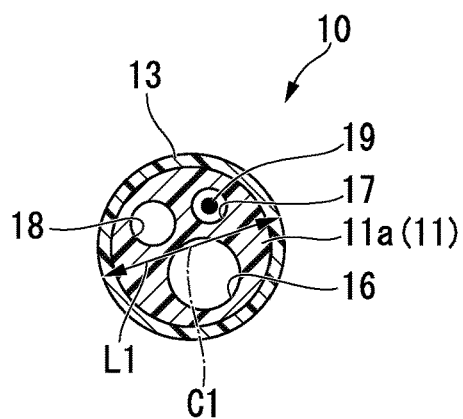
FIG. 4 is a cross-sectional view taken along line A2-A2 of FIG. 2.

As shown in FIGS. 2 to 4, the insertion section 10 has a sheath main body 11a constituting a proximal end side of a multi-lumen tube 11, a torque transmission member 12 installed at the sheath main body 11a, and a sandwiched portion 13 installed at a distal end side of the sheath main body 11a.

The multi-lumen tube 11 is formed of a resin such as PTFE (polytetrafluoroethylene) or the like, and three lumens 16, 17 and 18 extending along an axis C1 of the insertion section 10 are formed at the multi-lumen tube 11.

A guide wire lumen 16 has the largest diameter among the three lumens 16, 17 and 18, and a distal end thereof is opened. The guide wire lumen 16 is used for insertion of a guide wire (to be described below). A knife lumen 17 has the smallest diameter among the three lumens 16, 17 and 18, and a distal end thereof is sealed. A conductive wire 19 is inserted through the knife lumen 17. A solution sending lumen 18 has an open distal end, and has the second largest diameter among the three lumens 16, 17 and 18. The solution sending lumen 18 is used to send a solution such as a contrast medium or the like.

The torque transmission member 12 has a blade 22 formed of a metal and mounted on an outer circumferential surface of the sheath main body 11a, and a coating tube 23 configured to coat the blade 22.

As the blade 22, for example, a tubular shape obtained by binding a plurality of thin stainless steel wires and weaving the wires in a lattice shape, a tubular shape obtained by winding a set or a plurality of sets of stainless steel wire bands or stainless steel bands in a coil shape, or a tubular shape obtained by winding a set or a plurality of sets of coils in a plurality of layers while alternately changing winding directions may be used. The coating tube 23 may be formed of a resin having insulation.

The sheath main body 11a, the blade 22 and the coating tube 23 are fixed by an adhesive agent having softness such that they are bent even at a center of the channel of the curved endoscope and rotational torque is easily transmitted, constitute the coating tube 23 with a shrinkable tube having an inner diameter smaller than an outer diameter of the blade 22, or are configured by being softly adhered such that the blade 22 is likely to be bent with a shrinkable force of the coating tube 23.

When the sheath main body 11a, the blade 22 and the coating tube 23 are fixed, the distal end side of the insertion section 10 bent at a smaller radius by the endoscope is fixed with high softness and the proximal end side of the insertion section 10 bent at a relatively larger radius is fixed with a lower softness than the distal end side, a total rotational torque transmission property becomes better throughout the entire length of the insertion section 10.

The sandwiched portion 13 is constituted by an outer tube fixed to a distal end outer circumference of the sheath main body 11a. The proximal end side of the sandwiched portion 13 is fixed to the blade 22 while fitted onto the blade 22. An outer diameter of the proximal end side of the sandwiched portion 13 is substantially equal to an outer diameter of the coating tube 23. The sandwiched portion 13 may be formed of the same material as the coating tube 23, or may be formed of a material that cannot slide as easily as the material of the sheath main body 11a. For example, when the sheath main body 11a is formed of PTFE that can easily slide, FEP, PFA, polyamide, PET, a polyamide elastomer, a PET elastomer or the like may be more preferably used as the material of the sandwiched portion 13. A cross-section along a plane perpendicular to the axis C1 of the distal end side of the sandwiched portion 13 has a circular shape (see FIG. 4), and an outer diameter of the cross-section is L1. An outer diameter of the proximal end side of the sandwiched portion 13 may be larger than an outer diameter of the distal end side of the sandwiched portion 13.

The sandwiched portion 13 is configured such that the rotational torque is transmitted from the torque transmission member 12 to the sandwiched portion 13 because it is fixed to the blade 22.

The distal end section outer circumference of the torque transmission member 12 (the distal end section outer circumference of the coating tube 23) may be the sandwiched portion. In this case, the torque transmission member 12 extends from the proximal end side of the insertion section 10 to the sandwiched portion in the axis C1 direction.

As a separate method, the distal end section of the sheath main body 11a may be used as the sandwiched portion by expanding an outer diameter thereof through thermoforming.

Figure 5:
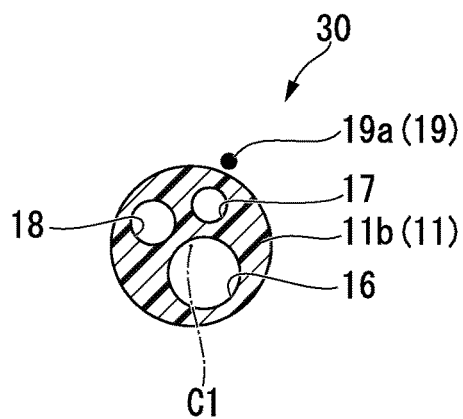
FIG. 5 is a cross-sectional view taken along line A3-A3 of FIG. 2.

As shown in FIGS. 2 and 5, the treatment section 30 has a knife support section 11b constituting the distal end side of the multi-lumen tube 11, and a knife section 19a constituted by the distal end section of the conductive wire 19.

Two transmission holes 11c and 11d formed from the inner circumferential surface of the knife lumen 17 to side surfaces of the knife support section 11b are formed in the knife support section 11b. The transmission holes 11c and 11d are formed at positions parallel to and spaced apart from each other in the axis C1 direction. A pre-curve (curl) may be formed at the knife support section 11b to be disposed inside of the curve when the opening formed in the outer surface of the knife support section 11b of the transmission holes 11c and 11d is curved. According to the above-mentioned configuration, the knife support section 11b can be easily inserted into the duodenal papilla.

The conductive wire 19 is extracted from the transmission hole 11c formed in the proximal end side of the knife support section 11b to the outside of the knife support section 11b, and pulled back into the knife lumen 17 again from the transmission hole 11d formed in the distal end side. A portion of the conductive wire 19 extracted from and exposed to the outside of the knife support section 11b becomes the above-mentioned knife section 19a used for treatment.

A distal end of the conductive wire 19 is fixed to the knife support section 11b via a chip 31 buried in the knife lumen 17.

In this way, the treatment section 30 is formed in a shape that is not rotationally symmetrical with respect to the axis C1 of the insertion section 10 (a rotationally asymmetrical shape).

The torque transmission member 12 has higher stiffness around the axis C1 than the sheath main body 11a or the knife support section 11b. That is, a rotational torque applied around the axis C1 is likely to be transmitted.

As shown in FIG. 2, the manipulation unit 40 has a manipulation unit main body 41 attached to the proximal end section of the insertion section 10, a rod-shaped handle 42 having a distal end attached to the manipulation unit main body 41, and a slider 43 slidably attached to the handle 42.

A guide wire cap 44 in communication with the guide wire lumen 16 and a solution sending cap 45 in communication with the solution sending lumen 18 are installed at the manipulation unit main body 41. A syringe (not shown) is detachable from the solution sending cap 45.

A ring 42a is attached to the proximal end section of the handle 42.

A terminal 43a electrically connected to the conductive wire 19 is installed at the slider 43. The terminal 43a can be connected to a high frequency power supply of the outside. A pair of rings 43b and 43c are attached to the slider 43 to sandwich the handle 42 therebetween.

The knife support section 11b is curved to stretch the knife section 19a by moving (returning) the slider 43 to the proximal end side with respect to the handle 42, the knife support section 11b can be formed in a linear shape, and the knife section 19a can be formed along the knife support section 11b by moving (cramming) the slider 43 to the distal end side with respect to the handle 42.

As shown in FIG. 1, as the endoscope 3, a known lateral vision type endoscope in which an endoscope manipulation unit 70 is installed at a proximal end of an endoscope insertion section 50 can be used. The endoscope insertion section 50 has a distal end hard section 56, a curving section 57 formed at the proximal end section of the distal end hard section 56 and configured to enable bending manipulation, and a flexible pipe section 58 formed at the proximal end section of the curving section 57. The distal end section of the channel 51 comes in contact with an opening 56a formed in the side surface of the distal end hard section 56.

In the channel 51 formed in the distal end hard section 56, a raising base 61 is attached to the distal end hard section 56 to be pivotable about a proximal end section thereof. A stopper 61s (see FIG. 6) abutting an edge section of the opening 56a of the distal end hard section 56 is installed at the raising base 61. In the case in which the raising base 61 is turned in a raising direction D1, when the stopper 61s abuts the distal end hard section 56, the raising base 61 cannot be further turned in the direction D1.

A manipulation wire 62 is connected to the distal end section of the raising base 61, and the proximal end section of the manipulation wire 62 extends to the endoscope manipulation unit 70 through the endoscope insertion section 50. The manipulation wire 62 is shown only in FIG. 1.

An illumination unit 56b having an LED or the like (not shown) and an observation unit 56c constituted by a CCD or the like (not shown) are installed at an edge section of the opening 56a of the distal end hard section 56 in a state in which they are exposed to the outside.

The illumination unit 56b and the observation unit 56c are connected to the endoscope manipulation unit 70 by a wiring (not shown).

A knob 71 configured to bend the curving section 57 and a lever 72 configured to advance and retract the manipulation wire 62 are installed at the endoscope manipulation unit 70. The knob 71 and the curving section 57 are connected by a curved manipulation wire (not shown), and the curving section 57 can be curved in a desired direction by manipulating the knob 71. The raising base 61 can be turned in the direction D1 to be raised by manipulating the lever 72 and returning the manipulation wire 62, and the raising base 61 can be turned in a direction D2 to be pushed down (laid down) by pressing the manipulation wire 62. Here, "the raising base 61 is completely raised" stated in the specification means that the raising base 61 is moved until the above-mentioned stopper 61s of the raising base 61 abuts the distal end hard section 56 and it cannot be turned in the direction D1.

Meanwhile, "the raising base 61 is raised" means that the raising base 61 is turned in the direction D1 regardless of whether or not the stopper 61s abuts the distal end hard section 56.

In the endoscope manipulation unit 70, a forceps stopper 73 is formed at the proximal end side of the channel 51, and comes in communication with the proximal end section of the channel 51. The forceps stopper 73 is formed of a material having elasticity such as rubber or the like. In the forceps stopper 73, in a natural state in which no external force is applied, as shown by an enlarged cross-sectional view of FIG. 1, a valve installed at the forceps stopper 73 is disposed at a position T1. Accordingly, leakage of a solution through the through-hole 73a of the forceps stopper 73 is prevented. When the insertion section 10 of the papillotome 2 is inserted into the through-hole 73a of the forceps stopper 73, as the valve is deformed to move to the position T2, the forceps stopper 73 reduces leakage of the solution from the channel 51 between the forceps stopper 73 and the insertion section 10 inserted into the through-hole 73a. Here, a frictional force is applied between the valve of the forceps stopper 73 and the insertion section 10.

A display unit such as a liquid crystal panel or the like, or a power supply, which is not shown, is connected to the endoscope manipulation unit 70 via a universal cord 75. The power supply is connected to the illumination unit 56b via the above-mentioned wiring, and the display unit is connected to the observation unit 56c via a wiring.

As an illumination method, a method of transmitting light of a lamp installed at a power supply to an illumination unit of a distal end of an endoscope by an optical fiber, instead of the illumination unit 56b, may be employed.

When the insertion section 10 is inserted into the channel 51 of the endoscope 3 configured as described above, a gap S is formed between the channel 51 and the insertion section 10. That is, hardly any frictional force is applied between the channel 51 and the insertion section 10.

Figure 7:
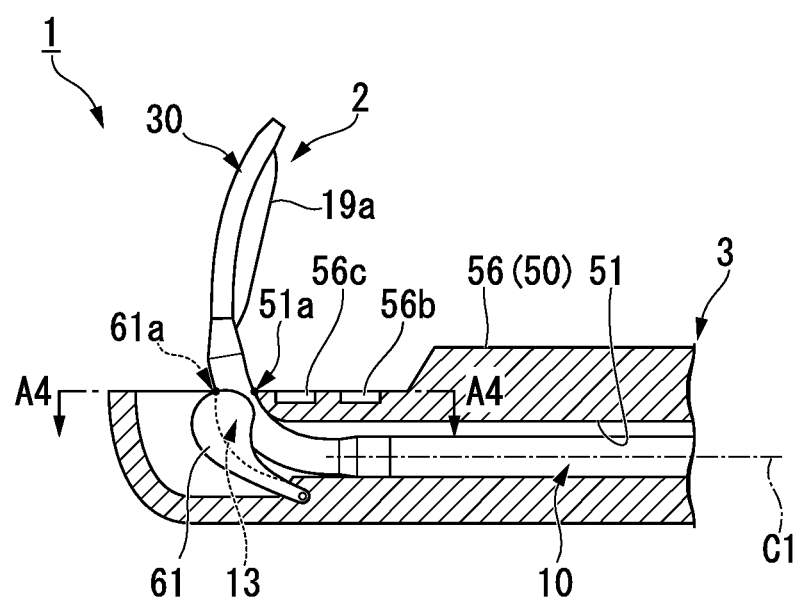
FIG. 7 is a cross-sectional view showing a state in which a sandwiched portion of the papillotome is sandwiched between the raising base and the channel when the raising base of the endoscope of the endoscope system is completely raised.
Figure 8:
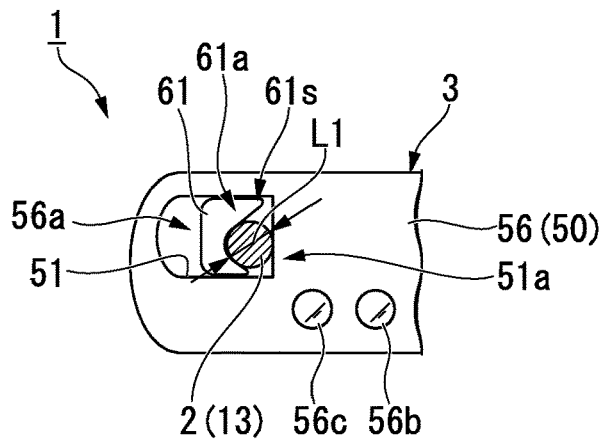
FIG. 8 is a cross-sectional view taken along line A4-A4 of FIG. 7.

As shown in FIGS. 7 and 8, the papillotome 2 inserts the insertion section 10 into the channel 51 of the endoscope 3, and adjusts a direction with respect to the axis C1 of the treatment section 30 as described above in a direction adjustment state in which the treatment section 30 protrudes from the distal end of the channel 51. In the direction adjustment state, the sandwiched portion 13 of the papillotome 2 is sandwiched between the raising base 61, which is completely raised, and the inner circumferential surface of the channel 51.

Figure 6:
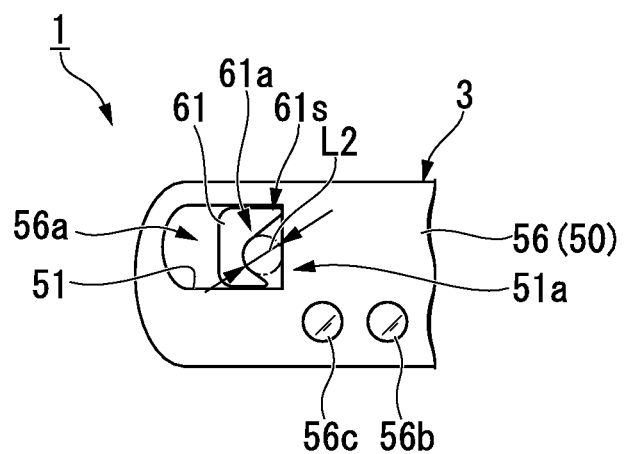
FIG. 6 is a view for describing a state in which a raising base is completely raised when the papillotome is not inserted through a channel of an endoscope of the endoscope system.

Here, as shown in FIG. 6, when the raising base 61 is completely raised without inserting the papillotome 2 through the channel 51 of the endoscope 3, a diameter of a maximum inscribed circle among inscribed circles between the raising base 61 and the inner circumferential surface of the channel 51, i.e., a diameter L2 of a maximum inscribed circle among inscribed circles between a portion 61a of the raising base 61 enclosing the sandwiched portion 13 and a portion 51a of the inner circumferential surface of the channel 51 enclosing the sandwiched portion 13, is defined. Here, an outer diameter L1 of the distal end side of the above-mentioned sandwiched portion 13 is larger than the diameter L2. An outer diameter of the proximal end side of the sandwiched portion 13 is larger than the outer diameter of the distal end side of the sandwiched portion 13. For this reason, the outer diameter of the proximal end side of the sandwiched portion 13 is larger than the diameter L2 of the maximum inscribed circle among the inscribed circles.

As shown in FIG. 8, when the sandwiched portion 13 of the papillotome 2 is sandwiched between the raising base 61, which is completely raised, and the inner circumferential surface of the channel 51, the stopper 61s does not abut the distal end hard section 56. The frictional force is applied between the inner circumferential surfaces of the raising base 61 and the channel 51, and the sandwiched portion 13.

Figure 9:
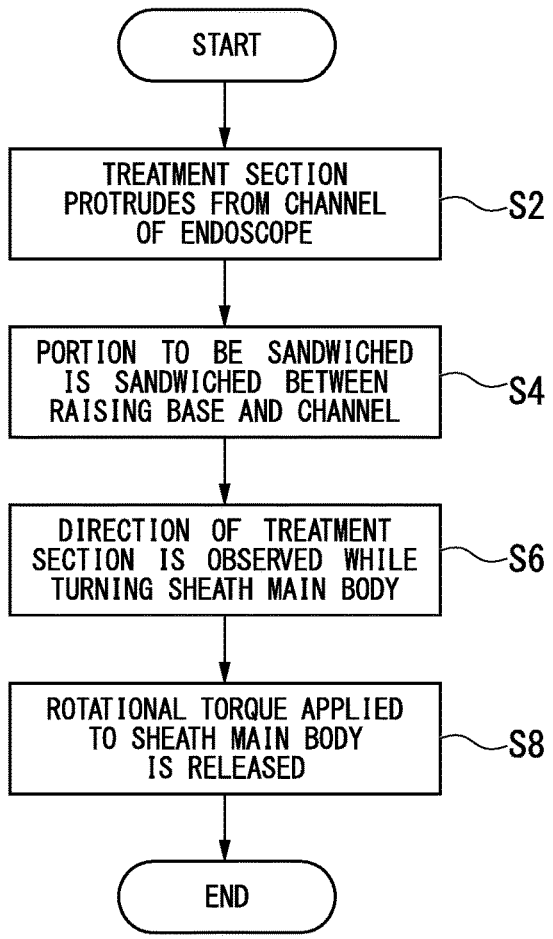
FIG. 9 is a flowchart showing a method of using the papillotome.

Next, a method of using the papillotome 2 configured as described above will be describing while exemplifying a procedure using the papillotome 2. FIG. 9 is a flowchart showing the method of using the papillotome 2.

Figure 10:
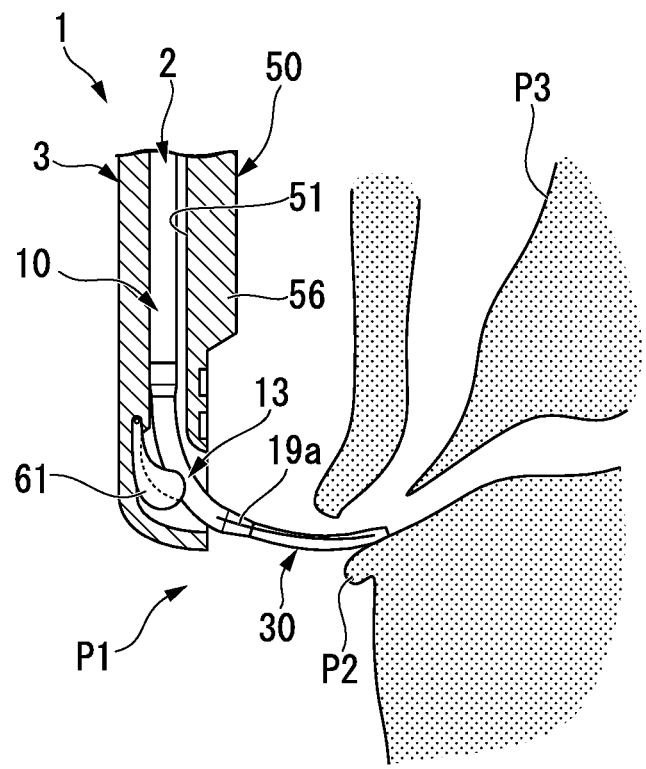
FIG. 10 is a view for describing a procedure of using the papillotome of the endoscope system.

First, power is supplied from the power supply to the illumination unit 56b, and surroundings of the illumination unit 56b are illuminated. An image of the reflected light is acquired by the observation unit 56c and converted into an electrical signal. The observation unit 56c transmits the converted electrical signal to the display unit via a wiring and the universal cord 75, and the image is displayed on the display unit. A user, who is an operator, manipulates the knob 71 as necessary while checking the image displayed on the display unit, and inserts the endoscope insertion section 50 of the endoscope 3 from a patient's mouth, which is a natural opening, while curving the curving section 57. As shown in FIG. 10, the endoscope insertion section 50 is introduced into the vicinity of the duodenal papilla P2 through the duodenum P1.

The insertion section 10 of the papillotome 2 is inserted into the channel 51 through the through-hole 73a of the forceps stopper 73 of the endoscope 3. A frictional force is applied between the valve of the forceps stopper 73 and the insertion section 10, and the forceps stopper 73 and the insertion section 10 are sealed in a substantially water-tight state. An insertion amount of the insertion section 10 is adjusted, and as shown in FIG. 10, the direction adjustment state in which the treatment section 30 protrudes from the distal end of the channel 51 starts (step S2 in FIG. 9).

The treatment section 30 is guided by the channel 51 and the raising base 61, and protrudes toward a side of the distal end hard section 56 of the endoscope insertion section 50. Accordingly, the distal end of the treatment section 30 is oriented in a direction of the bile duct P3 of the inner part of the duodenal papilla P2.

The distal end of the treatment section 30 is inserted into the duodenal papilla P2.

When a position of the bile duct P3 is recognized through X-ray photography, a contrast medium is injected into the solution sending lumen 18 from the syringe (not shown) mounted on the solution sending cap 45. The contrast medium is injected into the bile duct P3 through the solution sending lumen 18.

Figure 11:
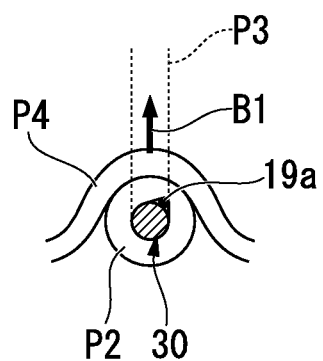
FIG. 11 is a view for describing disposition of the papillotome, the duodenal papilla and the bile duct in the image displayed on the display unit of the endoscope system.

The user recognizes a position of a headband fold P4 as shown in FIG. 11 with the image displayed on the display unit to determine an incision direction, and recognizes a current direction of the knife section 19a. Then, it is confirmed that a direction to be incised is determined as a twelve-o'clock direction shown by an arrow B1, and the direction of the knife section 19a is oriented in a two-o'clock direction.

Here, the user changes the direction of the knife section 19a from the two-o'clock direction to the twelve-o'clock direction, which will be described below.

Figure 12:
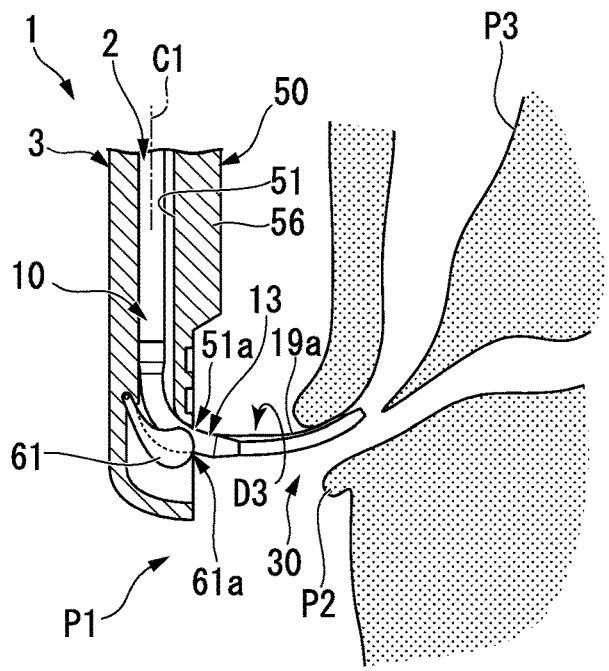
FIG. 12 is a view for describing a procedure of using the papillotome of the endoscope system.

First, the lever 72 is manipulated to completely raise the raising base 61 as shown in FIG. 12, and the sandwiched portion 13 of the insertion section 10 is sandwiched between the raising base 61, which is completely raised, and the inner circumferential surface of the channel 51 (step S4). Here, since the outer diameter L1 of the sandwiched portion 13 is larger than the diameter L2 of the maximum inscribed circle among the inscribed circles between the portion 61a of the raising base 61 and the portion 51a of the inner circumferential surface of the channel 51, a frictional force (a counter torque with respect to the rotational torque) is applied between the inner circumferential surfaces of the raising base 61 and the channel 51, and the sandwiched portion 13.

The user turns the torque transmission member 12 to one side E1 in the circumferential direction at the proximal end side of the torque transmission member 12 as shown in FIG. 2 by turning the manipulation unit 40 about the axis C1 of the insertion section 10. Accordingly, the torque transmission member 12 transmits the rotational torque input through the manipulation unit 40 by the user to the distal end side, and the sheath main body 11a is turned about the axis C1.

Since the frictional force is applied between the raising base 61, the channel 51 and the sandwiched portion 13, even when the user rapidly turns the manipulation unit 40, the sandwiched portion 13 is slowly turned about the axis C1 in a direction D3 with respect to the raising base 61 and the channel 51 as shown in FIG. 12. Here, a rotational torque is accumulated at the proximal end side more than the sandwiched portion 13 of the sheath main body 11a.

The user observes the direction with respect to the axis C1 of the treatment section 30 using the image displayed on the display unit of the endoscope 3 while turning the manipulation unit 40 and applying the rotational torque to the sheath main body 11a via the torque transmission member 12 (step S6).

When the direction of the knife section 19a of the treatment section 30 is a desired direction, i.e., the twelve-o'clock direction, the torque transmission member 12 is turned to the other side E2 of circumferential direction at the proximal end side of the torque transmission member 12 as shown in FIG. 2, and the rotational torque applied closer to the proximal end side than the sandwiched portion 13 of the sheath main body 11a is released (step S8).

The lever 72 is manipulated to pull down the raising base 61. The terminal 43a of the papillotome 2 is connected to the high frequency power supply. Fingers are appropriately inserted into the rings 42a, 43b and 43c of the manipulation unit 40 to grip the manipulation unit 40, and return the slider 43 to stretch the knife section 19a.

Figure 13:
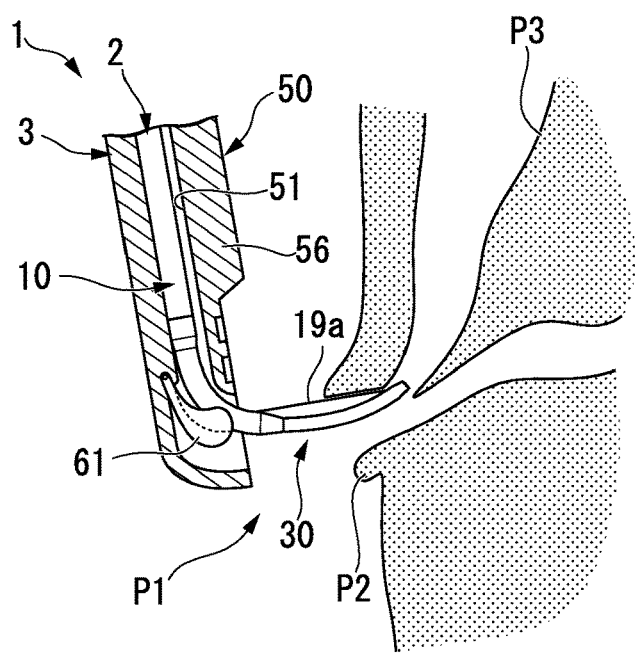
FIG. 13 is a view for describing a procedure of using the papillotome of the endoscope system.
Figure 14:
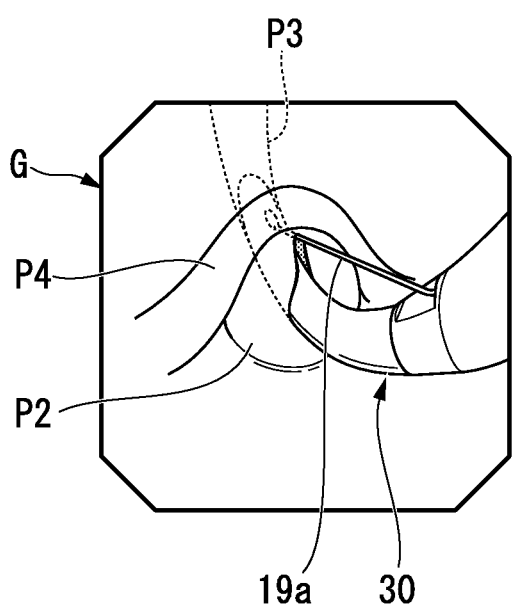
FIG. 14 is a view showing an example of the image in which the procedure of using the papillotome of the endoscope system is copied.

A high frequency current flows from high frequency power supply, and the lever 72 is manipulated to raise or pull down the raising base 61 to swing the treatment section 30. The high frequency current and a pressure from the tensile force of the knife section 19a are applied to the tissue of the duodenal papilla P2 in contact with the knife section 19a, and the duodenal papilla P2 is incised as shown in FIG. 13. For example, as shown in FIG. 14, since arrival at the desired incision amount is recognized through the image G of the display unit, electrical connection of the high frequency current is stopped.

Even when the direction to be incised is different from the twelve-o'clock direction due to an individual difference or the like of a patient, the direction of the knife section 19a of the treatment section 30 can be adjusted by the above-mentioned method.

When the incision of the duodenal papilla P2 is terminated, the slider 43 is pressed and moved from the knife support section 11b along the knife section 19a, and then, the papillotome 2 is removed.

Here, a basket forceps or the like (not shown) is inserted instead of the papillotome 2. The basket forceps is inserted into the bile duct P3 from the incised duodenal papilla P2 to catch the stones. The stones are broken when the stones are large, and the stones are discharged from the bile duct P3 as they are when the stones are small. When the stones are discharged, the basket forceps and the endoscope 3 are removed from the body.

As described above, according to the papillotome 2 and the endoscope system 1 of the embodiment, the insertion section 10 is inserted through the channel 51 of the endoscope 3, and the papillotome 2 enters the direction adjustment state in which the treatment section 30 protrudes from the channel 51. The lever 72 is manipulated to completely raise the raising base 61, and the sandwiched portion 13 is sandwiched between the raising base 61 and the inner circumferential surface of the channel 51. The direction with respect to the axis C1 of the treatment section 30 is observed by the endoscope 3 while turning the torque transmission member 12 to one side E1 in the circumferential direction. Since the frictional force is applied between the raising base 61, the channel 51 and the sandwiched portion 13, the treatment section 30 is slowly turned about the axis C1.

When the direction of the knife section 19a of the treatment section 30 is the twelve-o'clock direction, the torque transmission member 12 is turned to the other side E2 in the circumferential direction at the proximal end side of the torque transmission member 12. The rotational torque accumulated in the sheath main body 11a is released, and the direction of the treatment section 30 is fixed.

In this way, since the treatment section 30 is slowly turned, the treatment section 30 can be suppressed from being instantly turned at a timing unexpected by the user, time during which direction adjustment can be performed by the user can be increased, and the treatment section 30 can be accurately oriented in the desired direction with respect to the axis C1.

Here, when the material of the sandwiched portion 13 is a material that does not slide as easily as the material of the sheath main body 11a, ease of control of rotation of the insertion section 10 can be further increased while maintaining good insertion of the sheath main body 11a into the duodenal papilla P2.

In the embodiment, the distal end section outer circumference of the torque transmission member 12 may be the sandwiched portion as described above. In this case, the rotational torque transmitted to the proximal end side of the torque transmission member 12 can be effectively transmitted to the sandwiched portion in the axis C1 direction.

Second Embodiment

Next, a second embodiment of the present invention will be described with reference to FIGS. 15 to 26, in which elements that are the same as those of the first embodiment will be designated by the same reference numerals, description thereof will be omitted, and only different points will be described.

As shown in FIGS. 15 to 18, a papillotome 6 of the embodiment includes an insertion section 90, a treatment section 110 installed closer to the distal end side than the insertion section 90, and a manipulation unit 120 installed at the proximal end section of the insertion section 90 and configured to manipulate the treatment section 110.

Figure 19:
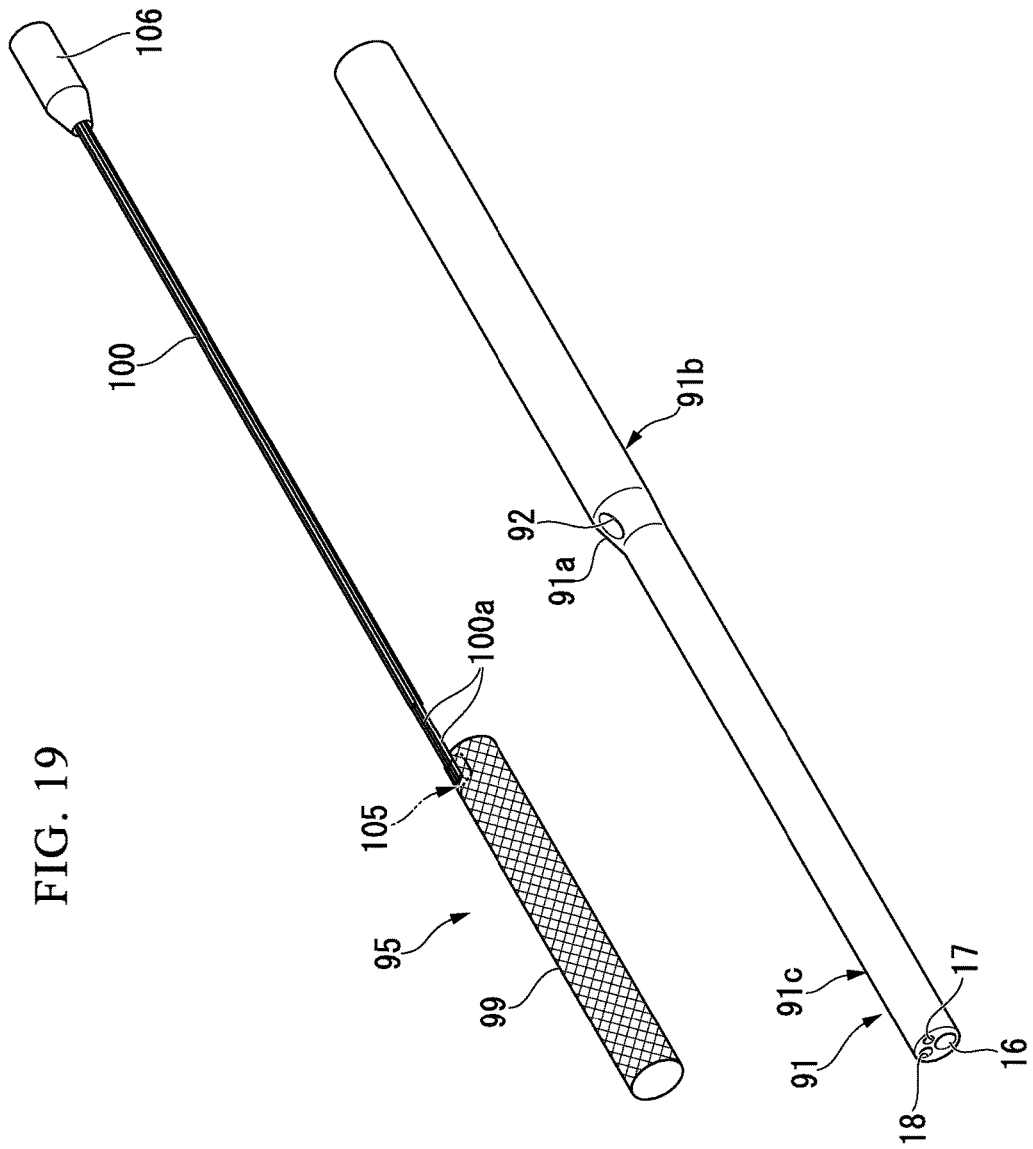
FIG. 19 is an exploded perspective view showing a multi-lumen tube and a torque transmission member used in the papillotome.

In the embodiment, a multi-lumen tube 91 as shown in FIG. 19 is used in the insertion section 90 and the treatment section 110. In FIG. 19, a coating tube 101 of a torque transmission member 95 (to be described below) is not shown.

In the multi-lumen tube 91, an outer diameter of the proximal end side is larger than an outer diameter of the distal end side, and a transition section 91a is formed at a boundary portion between the distal end side and the proximal end side. The above-mentioned three lumens 16, 17 and 18 are formed at the multi-lumen tube 91 throughout the entire length. A torque lumen (a lumen) 92 is formed at the multi-lumen tube 91 from the proximal end to the transition section 91a.

Figure 15:
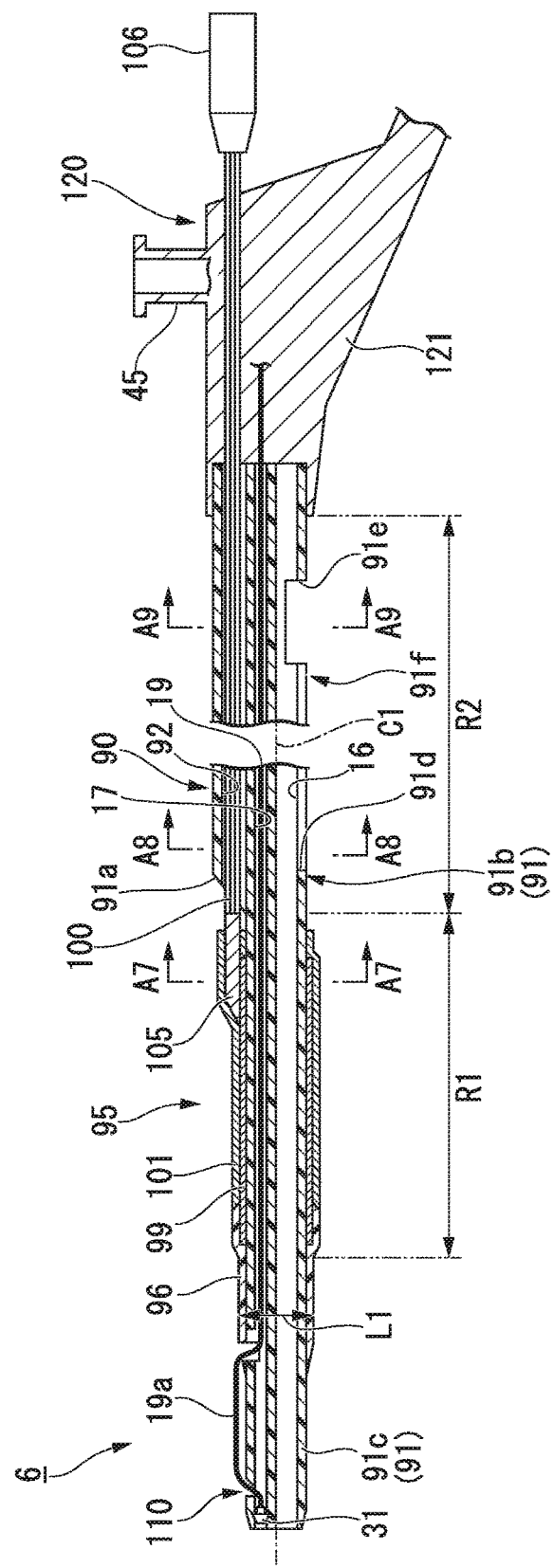
FIG. 15 is a side cross-sectional view schematically showing a papillotome of a second embodiment of the present invention.
Figure 17:
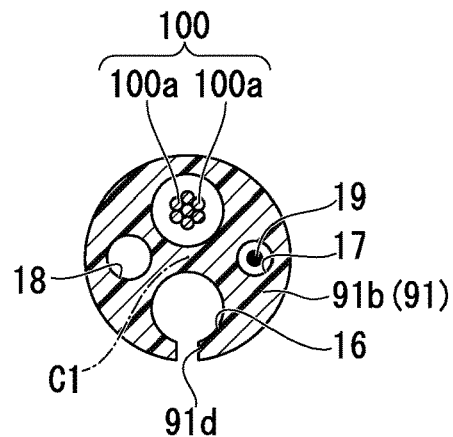
FIG. 17 is a cross-sectional view taken along line A8-A8 of FIG. 15.
Figure 18:
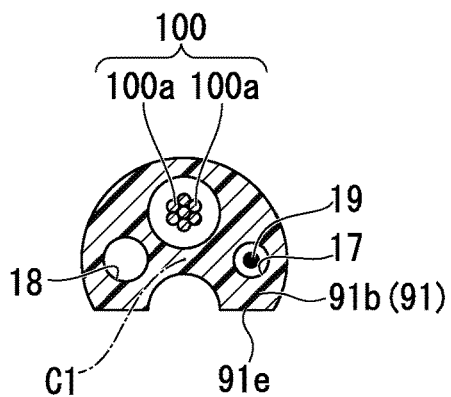
FIG. 18 is a cross-sectional view taken along line A9-A9 of FIG. 15.

The proximal end side from the intermediate portion between the distal end and the transition section 91a of the multi-lumen tube 91 is a sheath main body 91b, and the distal end side from the sheath main body 91b is a knife support section 91c. As shown in FIGS. 15 and 17, a narrow slit 91d reaching the outer circumferential surface of the sheath main body 91b is formed at the guide wire lumen 16 of the sheath main body 91b. The narrow slit 91d is formed throughout substantially the entire length of a separated sheath region R2 (to be described below) closer to the proximal end side than the transition section 91a. A width of the narrow slit 91d is formed to be slightly smaller than the outer diameter of a guide wire W (see FIG. 26) used in combination with the papillotome 6. A wide slit 91e having a larger width than the outer diameter of the combined guide wire W is formed at the proximal end of the narrow slit 91d.

A slit 91f is constituted by the wide slit 91e and the narrow slit 91d.

Figure 20:
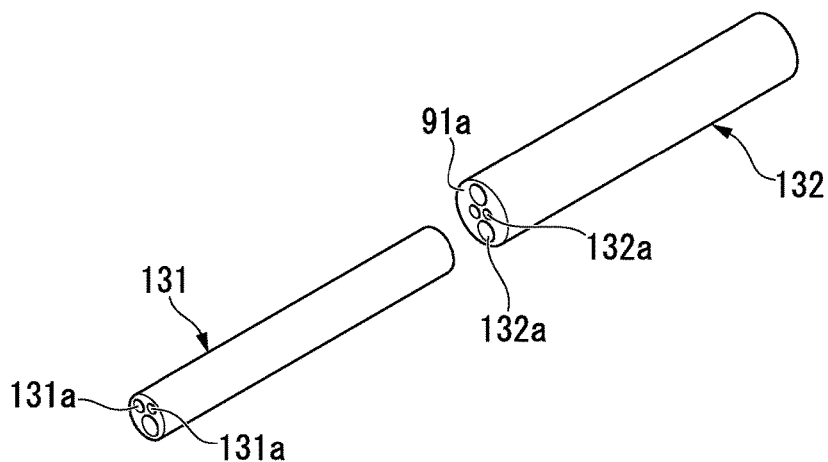
FIG. 20 is an exploded perspective view, in which the multi-lumen tube is divided into tube pieces, for describing a method of manufacturing the multi-lumen tube.

As shown in FIG. 20, the multi-lumen tube 91 may be formed by connecting tube pieces 131 and 132 separately manufactured before and after both sides of the transition section 91a. In this case, the multi-lumen tube 91 is configured by connecting the tube piece 131 of the distal end side at which three lumens 131a are formed and the tube piece 132 of the proximal end side at which four lumens 132a are formed.

Figure 21:
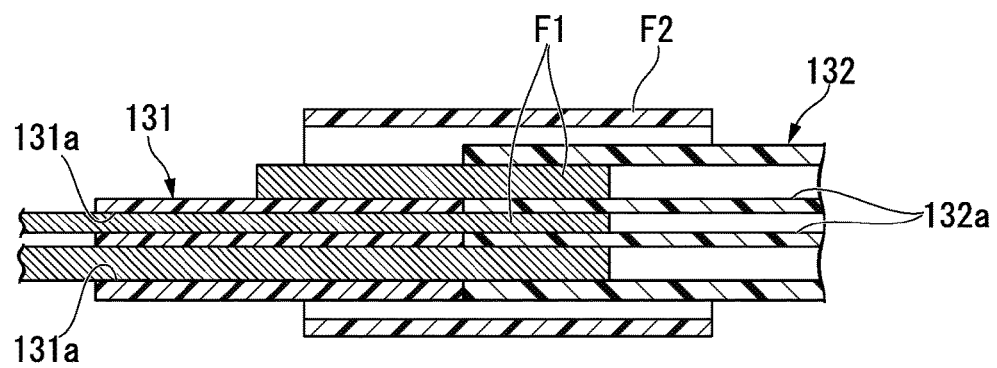
FIG. 21 is a cross-sectional view for describing a process of manufacturing the multi-lumen tube from the tube pieces.

As a method of connecting the tube pieces 131 and 132, a method that will be described below may be used. That is, as a first method, as shown in FIG. 21, one end side of a core bar F1 is inserted into the four lumens 132a of the tube piece 132, and the other end sides of three of the four core bars F1 are each inserted into one of the lumens 131a of the tube piece 131. End surfaces of the tube piece 131 and the tube piece 132 are matched. A heat-shrinkable tube F2 is covered outside the matched portion of the tube pieces 131 and 132.

Figure 22:
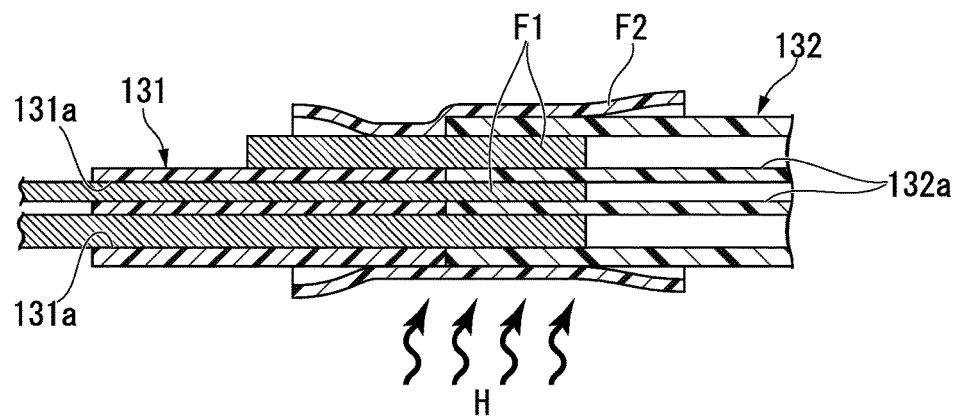
FIG. 22 is a cross-sectional view for describing a process of manufacturing the multi-lumen tube from the tube pieces.
Figure 23:
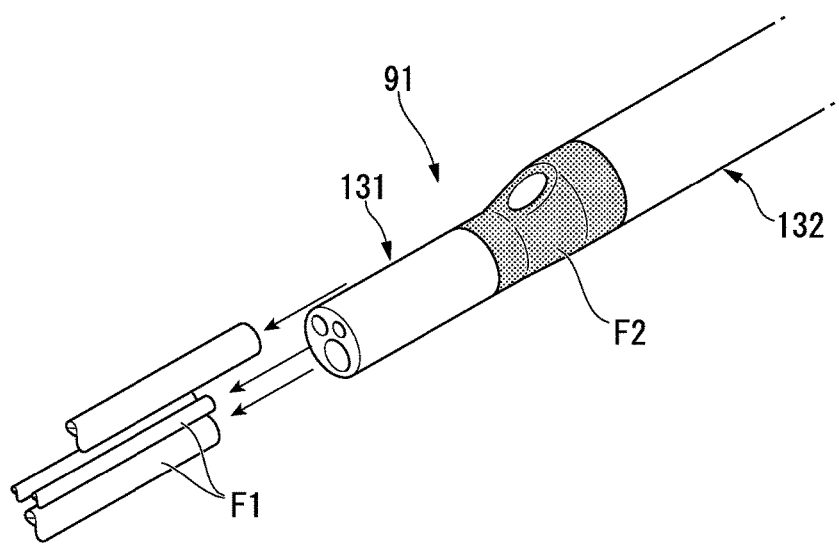
FIG. 23 is a perspective view for describing a process of manufacturing the multi-lumen tube from the tube pieces.

As shown in FIG. 22, as heat H is applied to the heat-shrinkable tube F2, the heat-shrinkable tube F2 shrinks to connect the tube pieces 131 and 132. After that, as shown in FIG. 23, the core bar F1 is removed from the tube pieces 131 and 132 of the multi-lumen tube 91.

Figure 24:
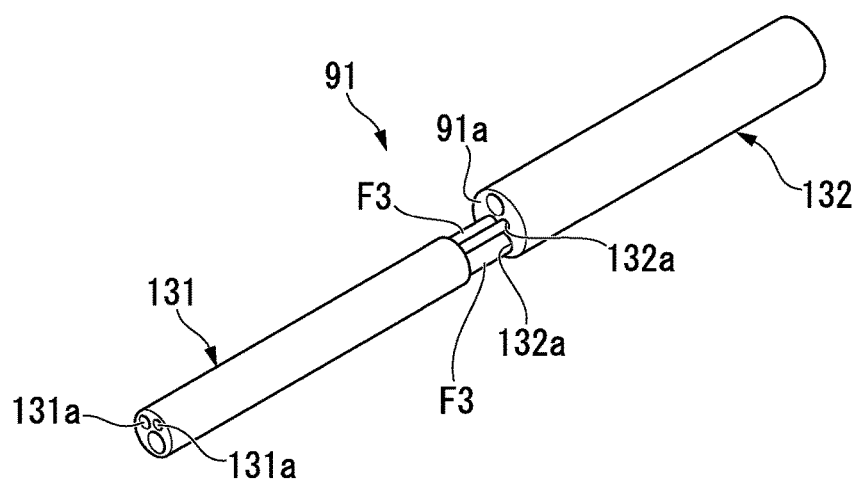
FIG. 24 is a perspective view for describing a process of manufacturing the multi-lumen tube from the tube pieces.

As a second method of connecting the tube pieces 131 and 132, as shown in FIG. 24, there is a method of configuring the multi-lumen tube 91 by press-fitting connecting pipes F3 into three of the four lumens 132a of the tube piece 132 and the three lumens 131a of the tube piece 131 and connecting the tube pieces 131 and 132.

In these methods of manufacturing the multi-lumen tube 91, since the tube pieces 131 and 132 are separately manufactured at the distal end side and the proximal end side of the transition section 91a, the tube pieces 131 and 132 can be manufactured of different materials. For example, since the heat is generated through incision with the knife section 19a of the treatment section 30, the tube piece 131 of the distal end side is manufactured of a fluorine resin (more specifically, PTFE) having high heat resistance, and the tube piece 132 of the proximal end side may be manufactured of polyamide, polyethylene, polypropylene or the like, which are inexpensive materials.

As shown in FIGS. 15 to 18, the insertion section 90 has the above-mentioned sheath main body 91b, the torque transmission member 95 installed at the sheath main body 91b, and a sandwiched portion 96 formed at the distal end side of the sheath main body 91b.

As shown in FIGS. 15 and 19, the torque transmission member 95 has a metal blade 99, a wire 100 having a distal end section fixed to the outer circumferential surface of the blade 99, and a coating tube 101 configured to coat the blade 99.

Figure 16:
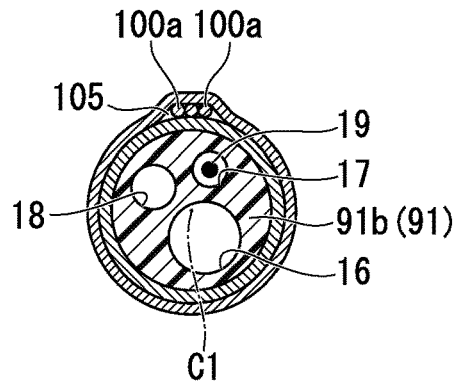
FIG. 16 is a cross-sectional view taken along line A7-A7 of FIG. 15.

The wire 100 is configured such that, in the embodiment shown in FIGS. 16 and 19, a plurality of element wires 100a are disposed parallel to the axis C1, and only the distal end and the rear end are fixed to each other through welding or the like. The element wire 100a may be formed of, for example, a stainless steel wire or a nickel titanium alloy.

Some of the plurality of element wires 100a extend to the distal end side and are fixed to the outer circumferential surface of the proximal end section of the blade 99 through welding as shown in FIG. 15. That is, the blade 99 and the wire 100 are fixed by a welding section 105. The welding section 105 is sandwiched between the proximal end section of the blade 99 and the proximal end section of the coating tube 101.

A grip 106 having a larger diameter than the wire 100 is fixed to the proximal end section of the wire 100.

The blade 99 and the coating tube 101 are formed in the same manner as the above-mentioned blade 22 and the coating tube 23.

Figure 25:
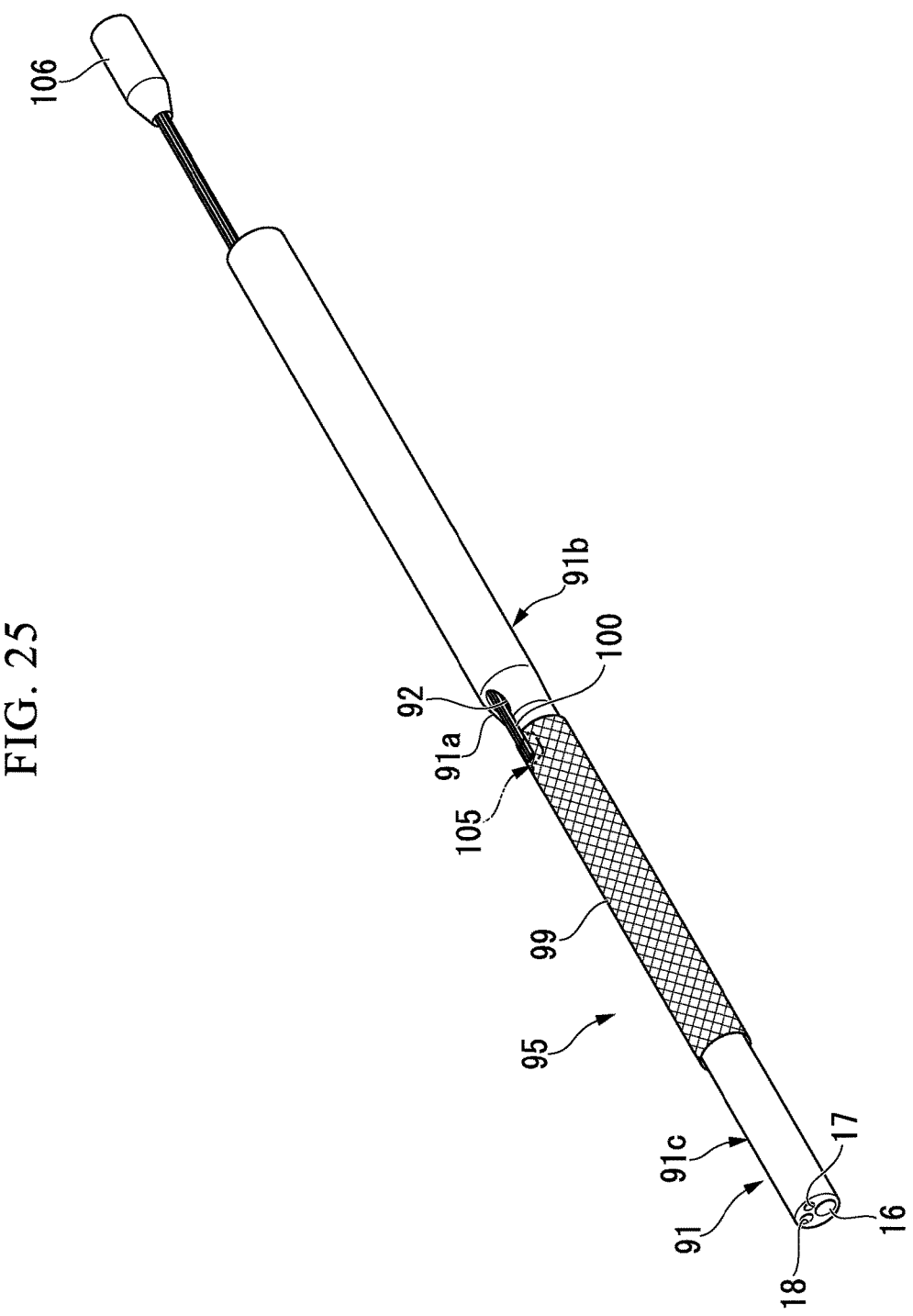
FIG. 25 is a perspective view showing a state in which the torque transmission member is attached to the multi-lumen tube.

The blade 99 and the wire 100 are attached (to be described below) to the multi-lumen tube 91 configured as described above. That is, as shown in FIG. 25, the blade 99 is fitted onto a portion of the sheath main body 91b closer to the distal end side than the transition section 91a, and fixed thereto by an adhesive material, a heat-shrinkable tube, or the like. The wire 100 to which the grip 106 is fixed is inserted from the proximal end side into a torque lumen 92 of the multi-lumen tube 91. The wire 100 protruding from the torque lumen 92 to distal end side is fixed to the blade 99 by the welding section 105.

The sheath main body 91b, the blade 99, and the coating tube 101 are fixed by the adhesive agent having softness to be bent in the middle of the channel of the curved endoscope and easily transmit the rotational torque, or the coating tube 101 is constituted by the shrinkable tube in which an outer diameter of the blade 99 is smaller than the original inner diameter, and they are configured to be softly adhered such that the blade 99 is easily curved by a shrinkable force of the coating tube 101.

As shown in FIG. 15, the sandwiched portion 96 is constituted by an outer tube fixed to the distal end outer circumference of the sheath main body 91b. The proximal end side of the sandwiched portion 96 is fixed to the blade 99 while fitted onto the blade 99. An outer diameter of the proximal end side of the sandwiched portion 96 is substantially equal to the outer diameter of the coating tube 101. The sandwiched portion 96 may be formed of the same material as the coating tube 101.

A cross-section by a plane perpendicular to the axis C1 of the distal end side of the sandwiched portion 96 has a circular shape, and an outer diameter of the cross-section is equal to the above-mentioned L1. An outer diameter of the proximal end side of the sandwiched portion 96 is larger than the outer diameter of the distal end side of the sandwiched portion 96.

As the sandwiched portion 96 is fixed to the blade 99, the rotational torque is transmitted from the torque transmission member 95 to the sandwiched portion 96.

In this example, while the sandwiched portion 96 is constituted by the outer tube, the distal end section outer circumference of the torque transmission member 95 (the distal end section outer circumference of the coating tube 101) may also be the sandwiched portion. As a separate method, the outer diameter of the distal end section of the sheath main body 91b may be increased through thermoforming to form the sandwiched portion.

The distal end side of the insertion section 90 is an integrated sheath region R1 to which the blade 99 and the coating tube 101 are attached outside the outer circumferential surface of the sheath main body 91b. Meanwhile, the proximal end side of the insertion section 90 is the separated sheath region R2 in which the wire 100 is pivotably manipulated in the torque lumen 92 of the sheath main body 91b while the wire 100 is not attached to the outside of the outer circumferential surface of the sheath main body 91b.

The portion of the multi-lumen tube 91 corresponding to the separated sheath region R2 is formed of a material having a smaller transmission force of the rotational torque than the torque transmission member 95, in other words, an easily twistable material.

The treatment section 110 has the same configuration as the treatment section 30 except that the knife support section 91c is used instead of the knife support section 11b in the treatment section 30 of the first embodiment.

A manipulation unit main body 121 of the manipulation unit 120 is formed such that the torque lumen 92 extends to the proximal end of the manipulation unit main body 121 with respect to the manipulation unit main body 41 of the first embodiment. The guide wire cap 44 in communication with the guide wire lumen 16 is not installed.

Figure 26:
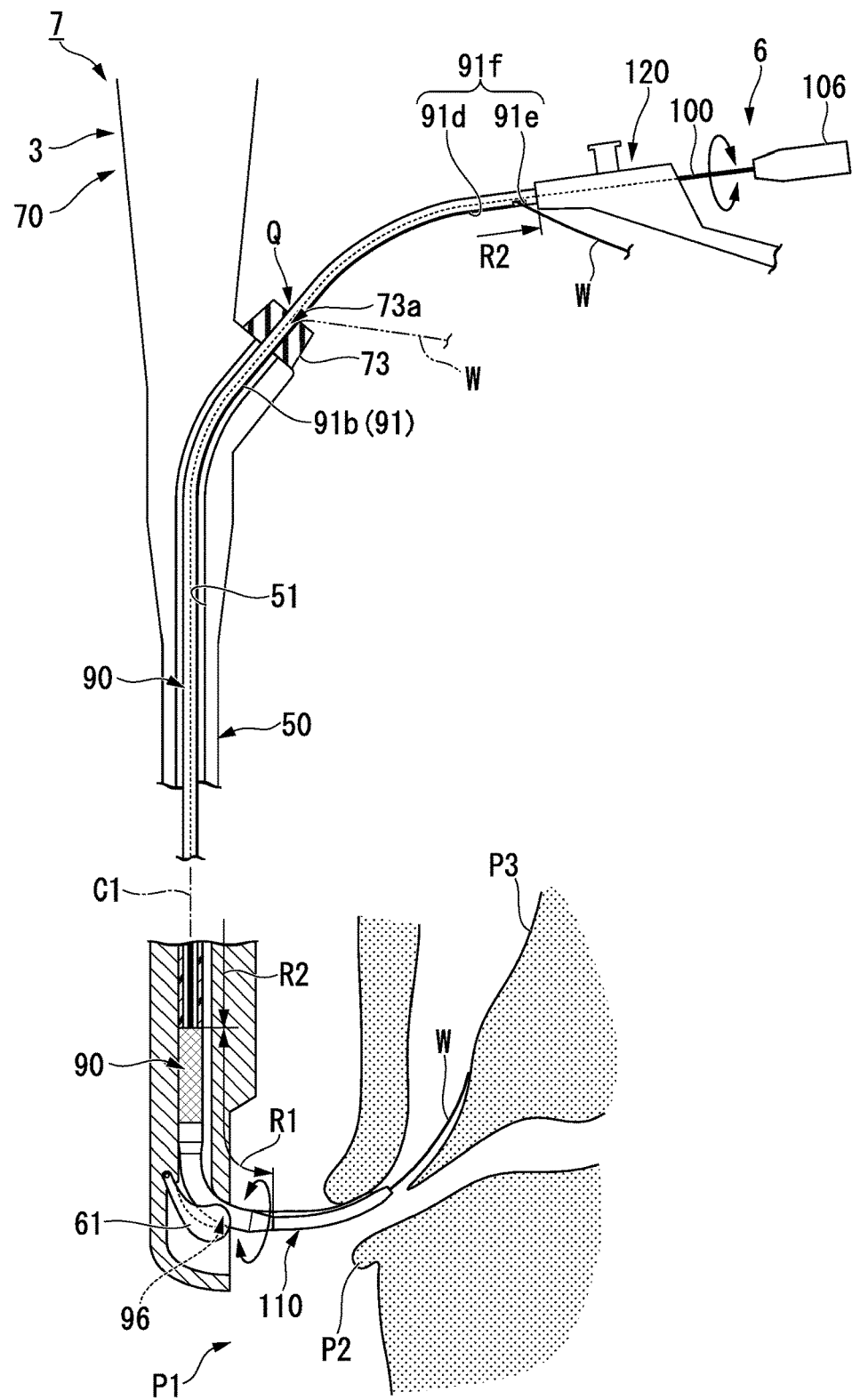
FIG. 26 is a view for describing a procedure of using the papillotome.

The papillotome 6 configured as described above is combined with the above-mentioned endoscope 3 as shown in FIG. 26 to constitute an endoscope system 7.

In the procedure using the papillotome 6, the guide wire W is inserted into the channel 51 through the through-hole 73a of the forceps stopper 73 of the endoscope 3. The portion of the insertion section 90 at which the narrow slit 91d is formed is inserted into the forceps stopper 73, and the wide slit 91e is disposed closer to the proximal end side than the forceps stopper 73. The guide wire W is introduced into the bile duct P3 through the duodenum P1.

The proximal end section of the guide wire W is inserted through the distal end of the guide wire lumen 16 of the papillotome 6, and the guide wire W is extracted to the outside from the wide slit 91e of the insertion section 90. The insertion section 90 of the papillotome 6 is inserted into the channel 51 through the through-hole 73a of the forceps stopper 73. When the insertion section 90 is inserted through the forceps stopper 73, the frictional force is applied between the valve of the forceps stopper 73 and the insertion section 90, and the forceps stopper 73 and the insertion section 90 are substantially water-tightly sealed.

The user adjusts an insertion amount of the insertion section 90 inserted into the channel 51 of the endoscope 3 to the direction adjustment state in which the papillotome 6 causes the treatment section 110 to protrude from the channel 51. Here, the insertion section 90 of the separated sheath region R2, i.e., the sheath main body 91b, is inserted through the forceps stopper 73. The frictional force is applied between the forceps stopper 73 and the sheath main body 91b of the separated sheath region R2.

When the grip 106 is turned about the axis C1, the rotational torque is transmitted to the blade 99 or the coating tube 101 via the wire 100 inserted through the torque lumen 92 of the sheath main body 91b, and transmitted to the integrated sheath region R1. Here, since the distal end of the separated sheath region R2 is connected to the proximal end side of the integrated sheath region R1 via the transition section 91a, the rotational torque is also transmitted to the separated sheath region R2 from the integrated sheath region R1. However, since the multi-lumen tube 91 is formed of an easily twistable material having a smaller transmission force of the rotational torque than the torque transmission member 95, the rotational torque applied to the distal end of the separated sheath region R2 is absorbed as the multi-lumen tube 91 is twisted. Accordingly, there is no need to rotate the manipulation unit main body 121 about the axis C1 by hand without transmission of the rotational torque to the manipulation unit main body 121.

Since the wire 100 is inserted through the torque lumen 92, an influence of the frictional force with respect to the rotational torque transmitted from the grip 106 by the forceps stopper 73 is suppressed.

When the distal end of the treatment section 110 is inserted into the duodenal papilla P2, the procedure becomes easy as the distal end of the treatment section 110 is inserted along the guide wire W.

The blade 99 or the coating tube 101 is turned with respect to the channel 51, and the direction of the treatment section 110 is changed.

As described above, according to the papillotome 6 and the endoscope system 7 of the embodiment, when the proximal end side of the insertion section 90 is turned about the axis C1, the treatment section 110 can be accurately oriented to the desired direction with respect to the axis C1.

When the papillotome 6 is in the direction adjustment state, the sheath main body 91b of the separated sheath region R2 is inserted through the forceps stopper 73, and the wire 100 is inserted through the torque lumen 92 of the sheath main body 91b. Accordingly, an influence of the frictional force with respect to the rotational torque transmitted to the wire 100 by the forceps stopper 73 is suppressed, and the rotational torque can be effectively transmitted to the distal end side of the torque transmission member 95.

Even when wire 100 is rotated to transmit the rotational torque to the torque transmission member 95, the rotational torque is not transmitted to the manipulation unit 120. Since there is no need to rotate the manipulation unit 120 corresponding to rotation of the wire 100, rotation manipulation of the manipulation unit 120 becomes easy.

Since the outer diameter of the wire 100 is smaller than the outer diameter of the blade 99 or the coating tube 101, in comparison with the portion at which the blade 99 or the like is formed, material cost of the torque transmission member 95 in the portion at which the wire 100 is installed can be reduced.

The slit 91f is formed at the guide wire lumen 16 of the sheath main body 91b in the separated sheath region R2. For this reason, the guide wire W passing through the guide wire lumen 16 is extracted to the outside from the slit 91f, and the procedure of inserting the insertion section 90 along the guide wire W can be easily performed.

The narrow slit 91d is formed to have a slightly smaller width than the outer diameter of the guide wire W. The multi-lumen tube 91 is elastically deformed because it is formed of a resin material, and the guide wire W can be extracted to the outside from the narrow slit 91d by elastically deforming the multi-lumen tube 91. As the position to which the guide wire W is extracted to the outside of the multi-lumen tube 91 is moved to a guide wire manipulation position Q (see FIG. 26) in the vicinity of the forceps stopper 73 in the narrow slit 91d, the user who manipulates the endoscope 3 can easily manipulate (press, retract, or the like) the guide wire W.

Even when the procedure is started only with the papillotome 6 and the guide wire W is inserted from the guide wire lumen on the way, since the narrow slit 91d is smaller than the outer diameter of the guide wire W, the guide wire W can be inserted into the distal end of the papillotome 6 while the guide wire W does not deviate to the outside in the middle of the narrow slit 91d.

In the embodiment, the wire 100 is configured such that plurality of element wires 100a are disposed along the axis C1 in parallel. However, the wire may be constituted by weaving the plurality of element wires 100a, or the wire may be constituted by a single wire. When the wire is constituted by the single wire, the distal end section of the wire may be cut in a flat plate shape, and the cut portion may be welded to the blade 99.

Hereinabove, while the first embodiment and the second embodiment of the present invention have been described in detail with reference to the accompanying drawings, the specific configurations are not limited to the embodiments but may include modifications, combinations, or the like, without departing from the spirit of the present invention. Further, it is needless to say that the elements described in the embodiments may be appropriately combined and used.

For example, in the first embodiment and the second embodiment, while the three or four lumens are formed at the sheath main body and the knife support section, at least one lumen may be formed there.

While the treatment instrument for the endoscope is the papillotome, the treatment instrument for the endoscope is not limited thereto.

For example, the treatment instrument for the endoscope may be a high frequency treatment instrument in which an L-shaped high frequency knife is formed at the distal end of the sheath section, or may be a grip forceps opened and closed by a pair of grip pieces. Even when the treatment instrument for the endoscope is configured as described above, the high frequency knife or the pair of grip pieces can be accurately oriented to the desired direction with respect to the axis of the sheath section.

The treatment section has a shape that is not rotationally symmetrical with respect to the axis C1. However, even if the treatment section has a rotationally symmetrical shape, when the tissue or the body fluid is attached to a portion of the treatment section in the circumferential direction during use of the treatment instrument for the endoscope and the tissue or the like is moved in the circumferential direction to use the treatment section, or the like, the present invention can be appropriately used.

The present invention further includes the following technical spirit.

(Additional Statement 1)

In a treatment instrument for an endoscope using a method in which the treatment instrument for an endoscope according to claim 1 is used in combination with an endoscope having a channel that is able to be inserted into the sheath section, the sheath section passes through the channel of the endoscope, and the treatment section protrudes from the channel, the sandwiched portion of the sheath main body is sandwiched between the raising base, which is completely raised, and the inner circumferential surface of the channel, as the torque transmission member is turned to one side in the circumferential direction at the proximal end side of the torque transmission member, the direction about the axis of the treatment section is observed by the endoscope while the sheath main body is turned about the axis of the sheath section to apply the rotational torque to the sheath main body, and when the treatment section is oriented in the desired direction, the torque transmission member is turned to the other side in the circumferential direction at the proximal end side of the torque transmission member, and the rotational torque applied closer to the proximal end side than the sandwiched portion of the sheath main body is released.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A treatment instrument for an endoscope used in combination with an endoscope, the treatment instrument comprising:
 a sheath having flexibility;
 a treatment section disposed at a distal end of the sheath; and
 a manipulation unit disposed at a proximal end of the sheath and configured to manipulate the treatment section,
 wherein the sheath comprises:
  a sheath main body having a lumen extending along a longitudinal axis of the sheath;
  a transition section comprising an opening in communication with the lumen, the opening located at an intermediate section of the sheath main body;
  a metal member fitted onto a distal portion of the sheath main body and the metal member covering a circumference of the sheath main body; and
  a wire, wherein the wire extends through the lumen of the sheath main body, wherein a distal end of the wire is protruded from the opening of the transition section and the distal end of the wire is fixed to a proximal end portion of the metal member, and the wire configured to transmit rotational movement of a proximal end of the wire to the metal member; and
 wherein the sheath main body comprises a first tube and a second tube, the second tube connected to a distal end of the first tube,
 the first tube comprises the lumen and the opening,
 the second tube is covered by the metal member,
 the first tube has a first center,
 the metal member has a second center, and
 the first center is offset from the second center,
 wherein the manipulation unit comprises:
  a manipulation main body fixed to a proximal end of the sheath main body; and
  a handle attached to a proximal end of the wire protruded from the manipulation main body and the handle being configured to input rotational torque to the wire,
 wherein the wire comprises a plurality of individual wires, and
 wherein the plurality of individual wires are only fixed to each other at each of a proximal end of the plurality of wires and a distal end of the plurality of wires.

2. The treatment instrument for the endoscope according to claim 1, wherein the metal member extends around the circumference of the sheath main body.

* * * * *